US007182743B2

(12) United States Patent
Slautterback et al.

(10) Patent No.: US 7,182,743 B2
(45) Date of Patent: Feb. 27, 2007

(54) ORTHOPEDIC NIGHT FOOT SPLINT

(75) Inventors: E. Gerald Slautterback, Coral Springs, FL (US); Rhonda Machin, Weston, FL (US); Daniel J. Bozza, Coral Springs, FL (US)

(73) Assignee: FLA Orthopedics, Inc., Miramar, FL (US)

( * ) Notice: Subject to any disclaimer, the term of this patent is extended or adjusted under 35 U.S.C. 154(b) by 75 days.

(21) Appl. No.: 10/851,810

(22) Filed: May 21, 2004

(65) Prior Publication Data

US 2004/0215123 A1 Oct. 28, 2004

Related U.S. Application Data

(63) Continuation-in-part of application No. 10/388,689, filed on Mar. 14, 2003, now abandoned, which is a continuation-in-part of application No. 29/177,120, filed on Mar. 4, 2003, now Pat. No. Des. 481,798.

(51) Int. Cl.
*A61F 5/00* (2006.01)
*A61F 13/00* (2006.01)
*A61F 5/37* (2006.01)

(52) U.S. Cl. ........................... 602/27; 602/16; 602/65; 128/882

(58) Field of Classification Search ............ 602/27–29, 602/16, 3, 23, 30, 60–62, 65, 66; 128/882, 128/869, DIG. 15, 893, 894; 2/22
See application file for complete search history.

(56) References Cited

U.S. PATENT DOCUMENTS 5,367,789 A * 11/1994 Lamont ....................... 36/9 R
5,445,603 A * 8/1995 Wilkerson ................... 602/27
5,486,157 A * 1/1996 DiBenedetto ................ 602/27
5,542,912 A * 8/1996 Hess .......................... 602/27
5,700,237 A * 12/1997 Hess .......................... 602/27
5,772,619 A * 6/1998 Corbett ....................... 602/16
5,776,090 A 7/1998 Bergmann et al.
5,799,659 A 9/1998 Stano
5,865,778 A * 2/1999 Johnson ...................... 602/27
5,887,591 A 3/1999 Powell et al.
5,897,520 A 4/1999 Gerig
6,019,741 A 2/2000 Prieskorn
6,102,881 A * 8/2000 Quackenbush et al. ....... 602/28
6,110,078 A 8/2000 Dyer
D434,504 S 11/2000 Miller
6,267,742 B1 7/2001 Krivosha et al.
6,361,514 B1 3/2002 Brown et al.
6,689,081 B2 * 2/2004 Bowman ..................... 602/27
6,824,523 B2 * 11/2004 Carlson ...................... 602/16
6,827,696 B1 * 12/2004 Maguire ..................... 602/27
6,858,017 B2 * 2/2005 Peters ........................ 602/27
2002/0128574 A1 * 9/2002 Darby ........................ 602/23
2005/0222531 A1 * 10/2005 Moore ........................ 602/27

* cited by examiner

*Primary Examiner*—Teena Mitchell
*Assistant Examiner*—Adam Brandt
(74) *Attorney, Agent, or Firm*—Gregory N. Clements; Clements / Walker

(57) ABSTRACT

A foot splint for the prevention and rehabilitation of plantar fasciitis by maintaining a wearer's foot and, hence, his plantar fascia, in a preselected amount of dorsiflexion. The foot splint includes a footplate for supporting the wearer's foot, a lateral strut extending along the lower leg of the wearer and having a strap for releaseably attaching the strut to the wearer's leg, and a wrap for wrapping around the foot of the wearer. A soft insole may be provided to cushion the wearer's foot from the footplate. The wrap, insole and footplate provide a comfortable "slipper-like" feel for the wearer. Moreover, the foot splint is particularly suited for use during sleep since it is light-weight and open configuration allows for the wearer to move unimpeded between sleep positions, resulting in a more restful sleep. Moreover, the lateral placement of the strut keeps the rigid portions of the foot splint from inadvertently abrading, striking, or otherwise interfering with the wearer's other leg.

14 Claims, 5 Drawing Sheets

22
80
20
10
12
16
18
14

10
12
14
16
18
20
24
30
34
40
42
46
50
52
60
62
66
78
82

ORTHOPEDIC NIGHT FOOT SPLINT

CROSS REFERENCE TO RELATED APPLICATION

This application is a continuation-in-part of utility application Ser. No. 10/388,689 filed on Mar. 14, 2003, now abandoned which itself was a continuation-in-part of design Application No. 29/177,120, filed Mar. 4, 2003.

FIELD OF THE INVENTION

The present invention generally to orthopedic devices for rehabilitating a human foot, and more particularly to a night splint for stretching the plantar fascia of a person for the treatment of plantar fasciitis.

BACKGROUND OF THE INVENTION

The plantar fascia is a ligament structure that attaches between the calcaneous bone of the heel and the metatarsals located in the front part of the human foot. In particular, the plantar fascia maintains the arch of the foot and is placed in tension during walking and running.

Traumatic or, more typically, chronic overstressing of the plantar fascia leads to a condition commonly referred to as “plantar fasciitis”. This condition is characterized by inflammation, as well as tearing and shortening of the plantar fascia through scarring. The inflammation and tearing usually occur at the point where the fascia is attached to the heel bone and can cause the growth of spike-like projections of new bone, called heel spurs.

The plantar fasciitis condition causes mild to severe pain in the heel or arch which, if left untreated, can interfere with walking and daily living activities, as well as athletic activity. This condition can afflict both athletic and sedentary persons, and is especially common in the obese and in people who exercise on hard surfaces.

The symptoms of plantar fasciitis usually occur in the morning, resulting from activity of the previous day, due to cramping and muscle tightening of the foot and leg at night while the individual is asleep. A broad range of treatments are prescribed for plantar fasciitis, depending upon the severity of the injury and length of time the condition has existed. Among commonly used treatments are rest, ice, anti-inflammatory/analgesia medication, ultrasound to decrease inflammatory response, taping, heel pads, support socks, orthopedic device, physical therapy and even surgery. The various orthosis include walking type splints, show insole inserts and night splints.

Although similar in appearance to foot and ankle casts, also called walking casts, a night splint for the treatment of plantar fasciitis is only superficially similar to a walking cast. A foot or ankle cast is made so that the force vector of the patient’s weight passes vertically through the cast and the patient’s leg when he is standing. In the medical industry, no walking casts are made which do not place the bottom of the patient’s foot at a 90 degree angle to the patients leg, which is consistent with a vertical force vector. Thus, no walking casts are built to induce and maintain dorsiflexion or plantar flexion. In addition, a walking cast is made to provide the patient with a weight-bearing region forward of the heel, on which the weight of the body is placed when walking, and from which the patient can pivot forward when taking the next stride. The bearing and pivoting structure can be a rounded knob under the mid region of the foot, or it can be a rounded surface which covers the bottom of the cast from heel to toe. A walking cast may also have a cushioning region directly under the heel to absorb some of the shock of walking. Walking casts are not made to wear in bed at night, and are not made to induce a stretching effect on tendons. They are made to provide support to healing ankle and foot joints and bones, and to control the motion of these healing joints and bones while healing takes place.

To treat plantar fasciitis, it is necessary to use considerable force to counteract the strong muscles and tendons of the lower leg and foot. If this force is applied improperly, pressure points can result, with resulting discomfort and complications for some patients. Some patients have reduced blood circulation or sensation in the feet, such as patients with diabetes, vascular insufficiency, polio, stroke, trauma, or neurological problems. In such patients, if they need to use a night splint for treatment of plantar fasciitis, it is important to minimize the pressure points exerted by the night splint on the patient’s foot, while still exerting the necessary force on the foot and lower leg structure. The night splint must also not bruise or scratch the collateral leg during sleep, must not soil or tear bedding, and must be compatible with a sleeping partner. Walking casts are not designed to accomplish these objects.

In contrast, night splints allow for rehabilitation of the plantar fascia by maintaining the foot in a dorsiflexed condition such that the plantar fascia is slightly extended and not allowed to contract during the night. Conventional night splints consist, essentially, of a boot-like structure which is strapped to a patent’s lower leg and foot. Although more streamlined than walking splints, boot-like splints are still quite heavy and bulky and, as such, are uncomfortable and interfere with sleep. For example, the boot splint impedes the wearer’s ease of moving between sleep positions. Moreover, the bulk of the splint may bruise or scratch the collateral leg during sleep, and may interfere with a sleeping spouse. Further, such splints encompass the ankle region of a person, and may exert pressure points on the patient’s foot or lower leg structure. Such pressure point concerns are even more critical for patient’s having reduced blood circulation or sensation in the feet, such as patients with diabetes, vascular insufficiency, polio, stroke, trauma, or neurological problems.

Another type of conventional night splint is a generally L-shaped brace. The top portion of the L-shaped brace is configured to fit around the rear and sides of the patient’s calf, ankle and heel, while the bottom portion of the L-shaped brace extends forwardly beneath the sole of the foot. These braces are held to the foot and leg by strapping, or the like. While such splints are less bulky than boot-type splints, some patients still complain that these splints are uncomfortable, particularly when worn in bed. The rigid portion of the splint is disposed between the patient and the bed mattress in most positions and, hence, can cause pressure points at the rear and side of the heel, ankle, and lower leg.

Another type of device for maintaining a dorsiflexion of the plantar fascia ligament is described in U.S. Pat. No. 5,399,155 issued to Strassburg et al. The device consists of an over-the-calf sock, a d-ring attached to the front (shin) side, and an adjustable support strap attached to the toe portion of the sock. The support strap is passed through the d-ring loop, and secures to itself utilizing hook and loop attachment. The degree of stretch provided to the to plantar fascia ligament can be controlled by adjusting the tension provided by the support strap. Such devices do not provide any lateral support for the foot. Furthermore, tension in the support strap tends to pull the sock down the leg of the wearer, which allows the foot to relax to plantarflexed position.

Accordingly, what is needed is a night splint for the rehabilitation of plantar fasciitis that is comfortable to wear during sleeping, while maintaining the plantar fascia in a slight stretch. Further needed is for the night splint to be light weight, streamline, and have a low profile, in order to enhance comfort to the wearer.

The Applicants are aware of the following U.S. patents concerning the treatment of plantar fasciitis:

| U.S. Pat. No. | Inventor | Issue Date | Title |
|---|---|---|---|
| 6,361,514 B1 | Brown et al. | Mar. 26, 2002 | UNIVERSAL ANKLE SPLINT |
| 6,267,742 B1 | Krivosha et al. | Jul. 31, 2001 | BIPLANAR FOOT DORSIFLEXION COLLAPSIBLE POSTERIOR SPLINT |
| 6,110,078 | Dyer | Aug. 29, 2000 | PASSIVE STRETCHING DEVICE FOR PLANTAR FASCIA |
| 6,109,741 | Prieskom | Feb. 1, 2000 | ORTHOPEDIC FOOT SPLINT |
| 5,897,520 | Gerig | Apr. 27, 1999 | UNITARY DORSAL NIGHT SPLINT |
| 5,887,591 | Powell et al. | Mar. 30, 1999 | RESTRAINT AND METHOD FOR THE IMPROVED TREATMENT OF RECALCITRANT PLANTAR FASCIITIS |
| 5,799,659 | Stano | Sep. 1, 1998 | ANKLE FOOT ORTHOSIS NIGHT SPLINT WITH ORTHO WEDGE |
| 5,776,090 | Bergmann et al. | Jul. 7, 1998 | MEANS AND METHOD FOR TREATING PLANTAR FASCIITIS |
| Des. 434, 504 | Miller | Nov. 28, 2000 | NIGHT SPLINT FOR A FOOT |

SUMMARY OF THE INVENTION

The present invention is an orthosis foot splint for treatment and rehabilitation of plantar fascia. The foot splint is configured to maintain a wearer's foot in slight dorsiflexion in order to stretch the plantar fascia. The foot splint is light-weight, streamline, and avoids causing pressure points against the wearer's foot and leg, thus making the splint comfortable and unobtrusive to wear while resting in bed.

In addition to its use in the treatment of plantar fasciitis, the invented foot splint can be used in the treatment of calf muscle cramps, muscle tightening and runner's cramps, foot drop, paratenon tendonitis, achilles tendonitis, heel and arch pain, pronation syndromes, calcaneal apophysitis, and post-surgical treatment of the foot.

In the broadest sense, the present invention relates to a foot splint having a footplate and a strut. The footplate and lateral strut are attached together and hold a wearer's foot in an angle in dorsiflexion. Preferably, the strut includes an opening that coincides with the ankle of the wearer to provide additional comfort to the wearer. More preferably, the strut is positionable along the lateral side of the wearer's leg.

OBJECT OF THE INVENTION

The principal object of the present invention is to provide an orthosis device facilitates rehabilitation of a patient's foot from plantar fasciitis.

Another object of this invention is to provide an orthosis device that maintains the plantar fasciitis of a patient in slight tension.

A further object of this invention is to provide an orthosis device that is selectably adjustable between different degrees of dorsiflexion.

Another object of this invention is to provide an orthosis device that is lightweight.

Still another object of this invention is to provide an orthosis device that is not bulky and has a low profile.

A further object of this invention is to provide an orthosis device that is comfortable to wear while resting in bed.

BRIEF DESCRIPTION OF THE DRAWINGS

The foregoing and other objects will become more readily apparent by referring to the following detailed description and to the appended drawings in which.

DETAILED DESCRIPTION

The present invention is a device for maintaining the plantar fascia in a slight stretch for the rehabilitation and relief from plantar fasciitis. The device is uniquely configured for comfortable wear during sleeping.

Figure 1:
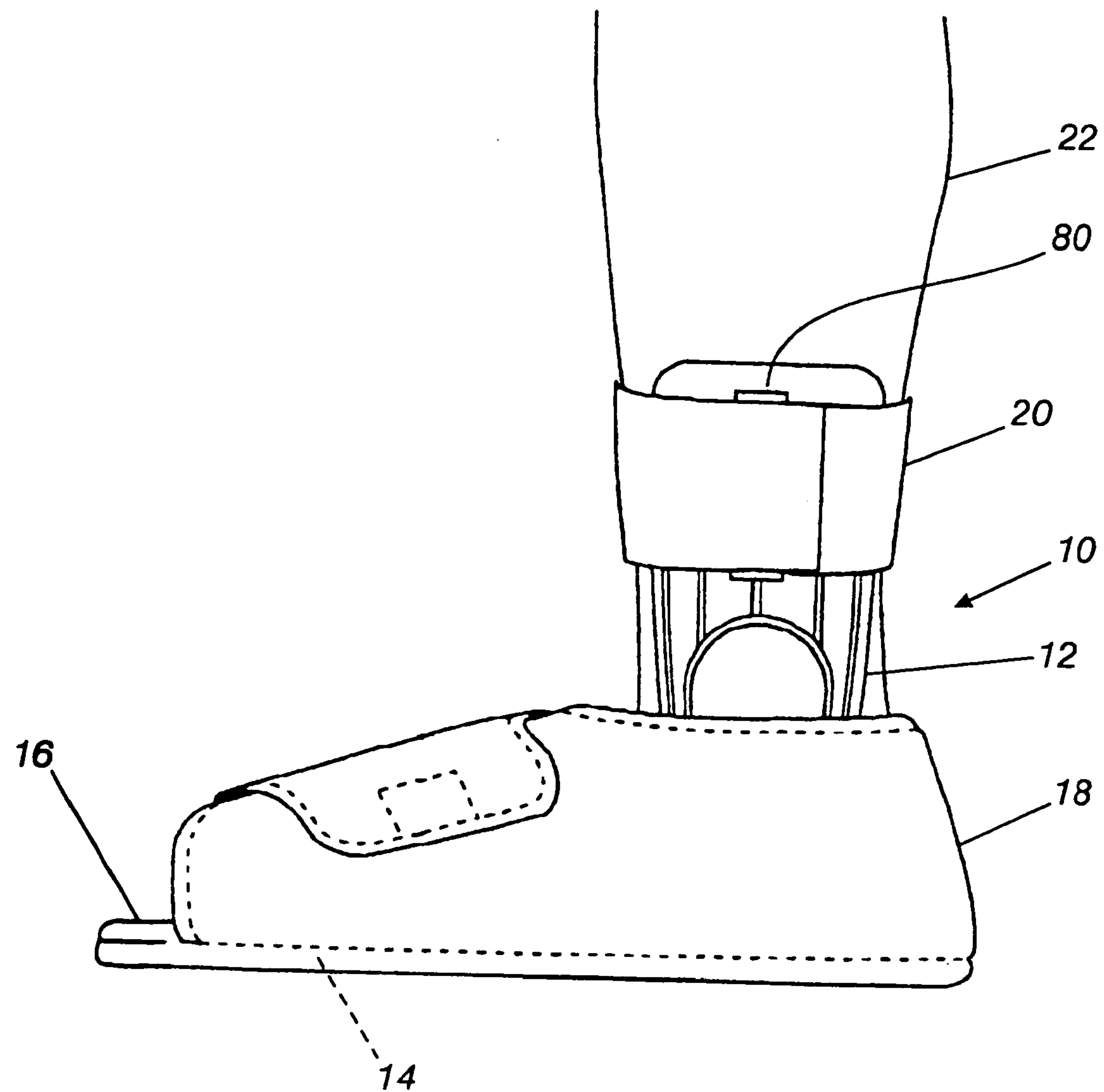
FIG. 1 is a side view of the invented foot splint, taken from the lateral side of a wearer's foot, in position on the wearer's left foot.

Referring now to the drawings, and particularly to FIG. 1, the invented foot splint 10 is shown in position on a wearer's foot, here the left foot. The foot splint 10 includes a lateral strut 12 attached to a footplate 14, a soft insole 16 for providing a cushioning barrier between the foot and the footplate 14, a soft wrap 18 for holding the foot in place to the footplate 14, and a strap 20 for holding the lateral strut 12 in place on the wearer's leg 22.

Figure 2:
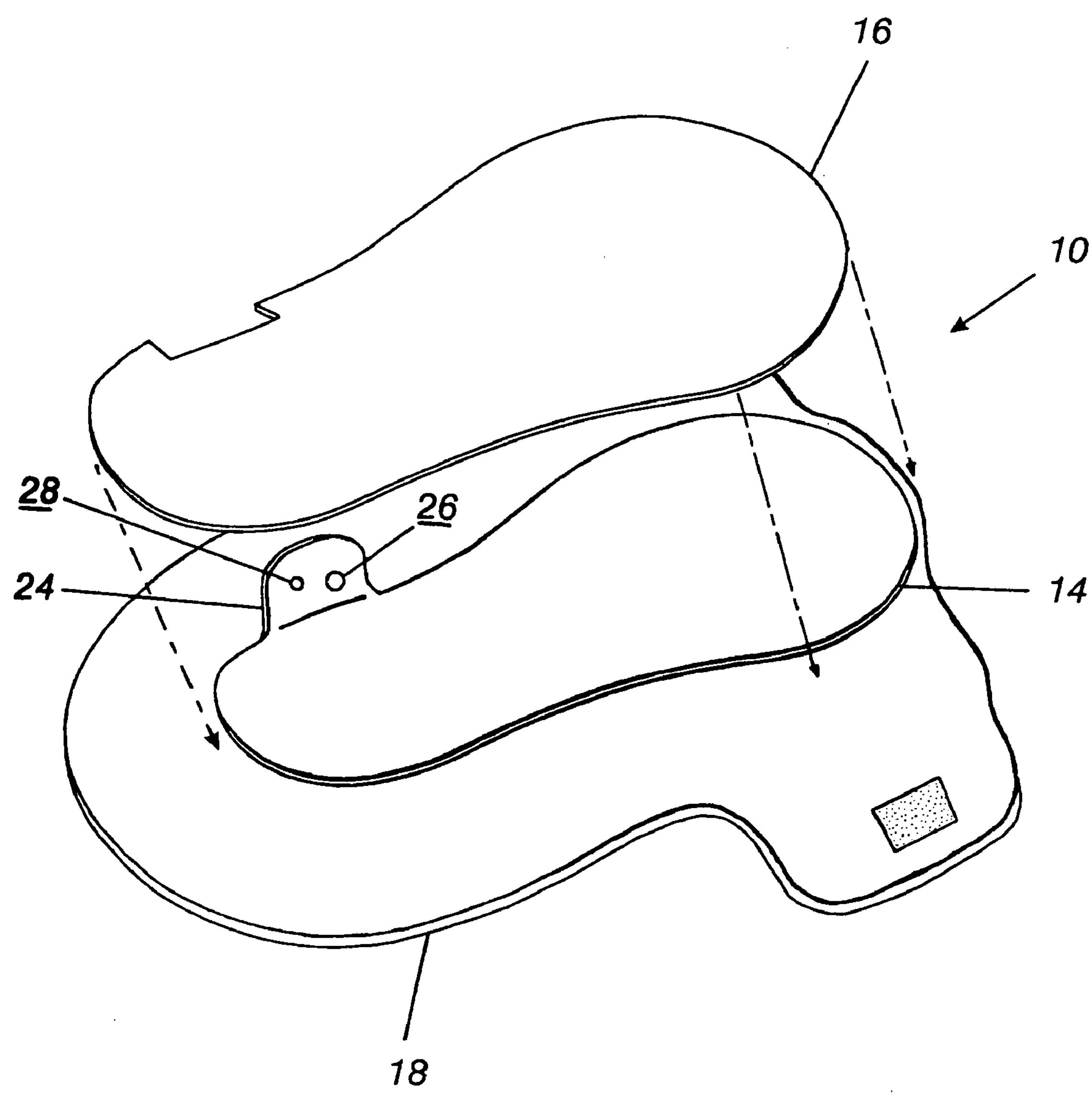
FIG. 2 is an exploded perspective view of the foot splint of FIG. 1, partially constructed, shown without a lateral strut.

FIG. 2 shows the foot splint 10, partially constructed, with the wrap 18 laid open and the strut removed in order to illustrated further details of the invention. The footplate 14 is shaped and sized so that the wearer's foot may be fully supported thereon. The footplate 14 is also sufficiently rigid in order to support the wearer's foot.

A bracket 24 extends from the lateral side of the footplate 14 and forms the mounting to which the lateral strut 12 (FIG. 1) is attached. The bracket 24 is provided with a pivot hole 26 and a set opening 28. The pivot hole 26 defines the pivot axis between the footplate 14 and the strut 12, while the set opening 28 allows for the foot splint 10 to be set at selected degrees of dorsiflexion, as further described below.

The soft insole 16 is sized and laid over the footplate 14 to provide a cushioning barrier between the wearer's foot and the footplate 14. In the preferred embodiment, the periphery of the insole 16 slightly overhangs the edges of the footplate 14. Stitching 30 is provided through this periphery and joins the insole 16 to the wrap 18, as shown in FIG. 3.

The wrap 18 has a portion that is positioned under the footplate 14, and side portions which conform around the sides of the wearer's foot. The bottom portion of the wrap 18 provides a cushioning barrier between the footplate 14 and the surrounding environment. The heel portion 46 of the wrap 18 may be cupped to hold the heel of the wearer's foot. A flap portion 34 of the wrap 18 is sized to extend over the top of the foot, to the other side of the wrap 18, where it is releasably attachable thereto by complementary Velcro™-type hook and pile fasteners 40, 42. The wrap 18, and particularly the flap portion 34, securely holds the wearer's foot in place against the footplate 14. The wrap 18, by generally conforming to the foot, gives the foot splint 10 a non-bulky, low profile structure. Advantageously, the wrap 18, insole 16 and footplate 14 form a comfortable, slipper-like foot enclosure.

It is noted that other means may be used to secure the wrap 18 over the foot. For example, the outer surface of the wrap 18 may be made of a Lycra™ spandex and nylon blend having an unbroken loop construction to which the Velcro™-type hooks 40 provided on the flap portion 34 may be frictionally engaged. As another example, complementary snaps, zipper or laces may be used. However, as these attachment means are more cumbersome to use, limit the amount that the wrap can be adjusted to accommodate various foot sizes, or may cause pressure points and ridge lines and, thus, they are not preferred. As it will also be appreciated by those skilled in the art, the wrap 18 may be provided in a variety of configurations. For example, the wrap 18 may be configured so that it extends only along the sides and top of the wearer's foot, and not under the footplate 14.

Figure 3:
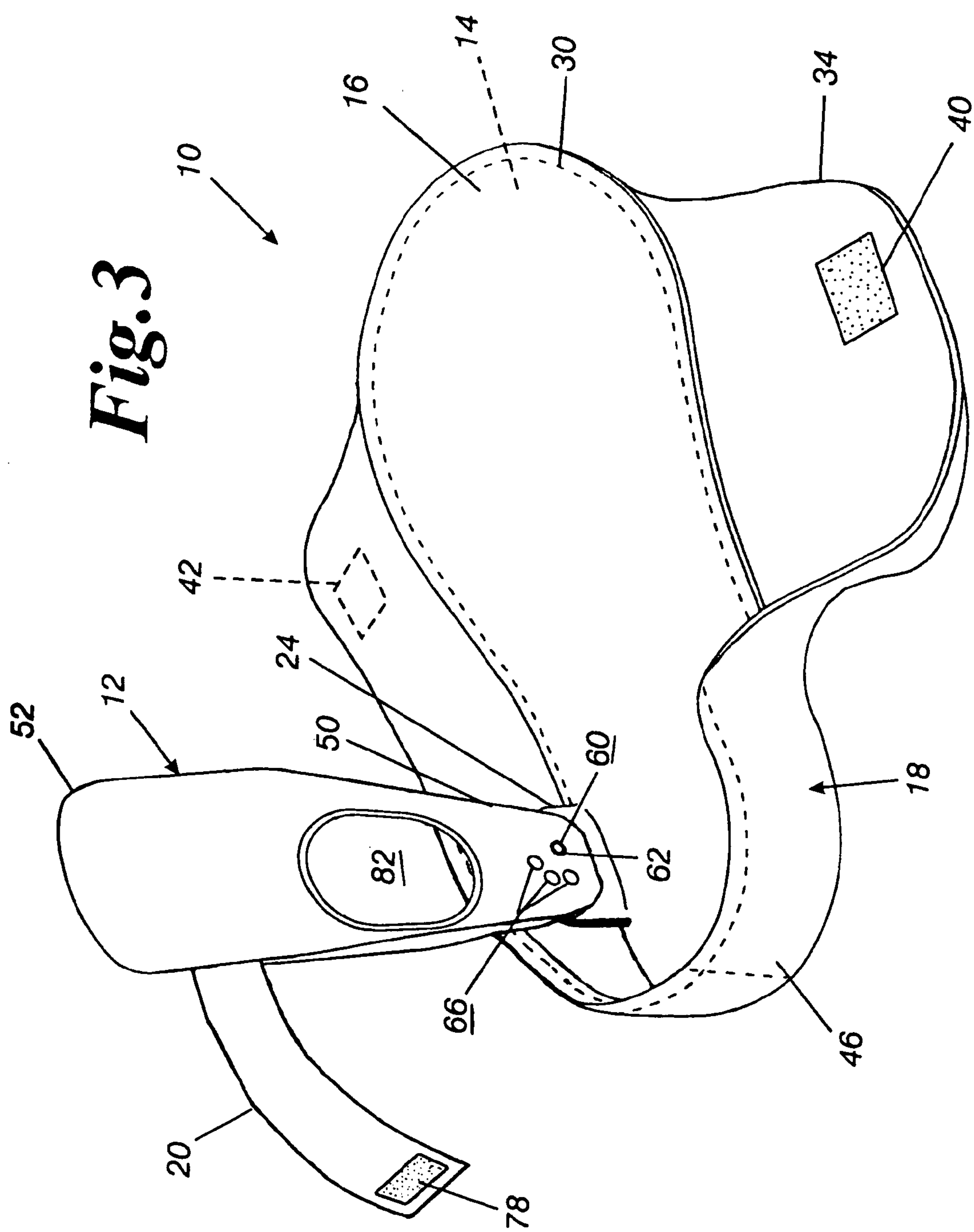
FIG. 3 is a perspective view of the foot splint of FIG. 1, with the wrap open to receive the left foot of a wearer.

FIG. 3 shows the foot splint 10 in completed form, with the lateral strut 12 in place, and ready to receive the left foot of a wearer. The strut 12 extends along the lateral side of the wearer's leg and has a distal section 50 attached to the footplate bracket 24 and a proximal section 52 terminating along the wearer's lower leg. A cushioning material (not shown) may be attached to the inward facing surface of the strut 12 to form a soft barrier between the strut 12 and the wearer.

The distal section 50 of the strut 12 is provided with a pivot hole 60, which corresponds to the bracket pivot hole 28 (FIG. 2). A pivot 62 is received through the pivot holes, rotatably mounting the strut 12 to the footplate 14. The distal section 50 is also provided with a plurality of radially spaced set openings 66 which may be aligned with the set opening 28 (FIG. 2) in the bracket 24 by rotating the strut 12 in relation to the footplate 14 until the desired set openings are aligned. A set screw 68 (FIG. 4), pin with a spring loaded detent, or other suitable means, may be inserted through the selected set openings to fix the desired amount of dorsiflexion in which the foot splint 10 is to be placed. That is, the footplate 14 and strut 12 may be selectively set at an acute angle in relation to each other. As an example, the illustrated set openings 66 allow for the foot splint 10 to be adjusted in 5 degree increments between 80 and 90 degrees in order to hold the wearer's foot in slight dorsiflexion. As such, the wearer can adjust the amount of desired "stretch" at which to maintain his plantar fascia.

Optionally, the lateral strut 12 may be provided with a malleolus opening 82. The malleolus opening 82 is sized and formed in the lateral strut 12 to coincide with the ankle bone of the wearer. As such, any potential pressure points between the strut 12 and ankle are obviated.

The strut 12 is releasably secured to the wearer's leg by the strap 20. The strap 20 is affixed at one end to the strut 12, and has a sufficient length so that the free end can be wrapped around the lower leg of the wearer, tensioned to the leg an appropriate amount, and attached to the strut 12 via frictionally mating Velcro™-type hook and pile fasteners 78, 80 (see also FIG. 1).

Figure 4:
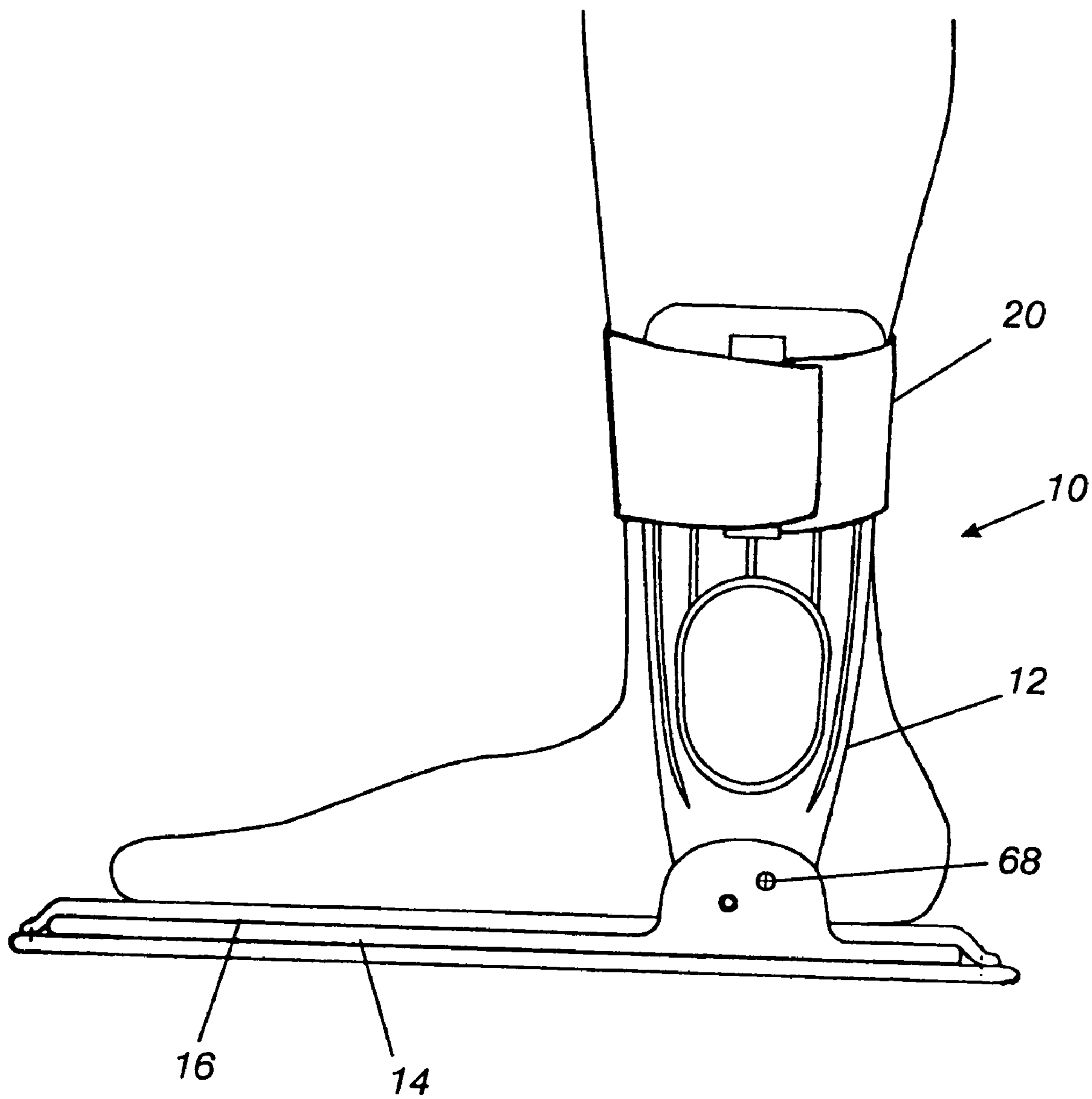
FIG. 4 is a side view of the foot splint of FIG. 1, with the sides of the wrap removed for illustrative purposes.

In FIG. 4, the foot splint 10 is shown with the sides of the wrap 18 removed for illustrative purposes. As shown, the foot is held along the footplate 14, with the insole 16 providing cushioning there-between. The lateral strut 12 extends along the lateral side of the leg and is releaseably attached thereto by the strap 20. The set screw 68 is shown inserted through the selected set openings to set the desired amount of dorsiflexion for the foot splint 10.

Figure 5:
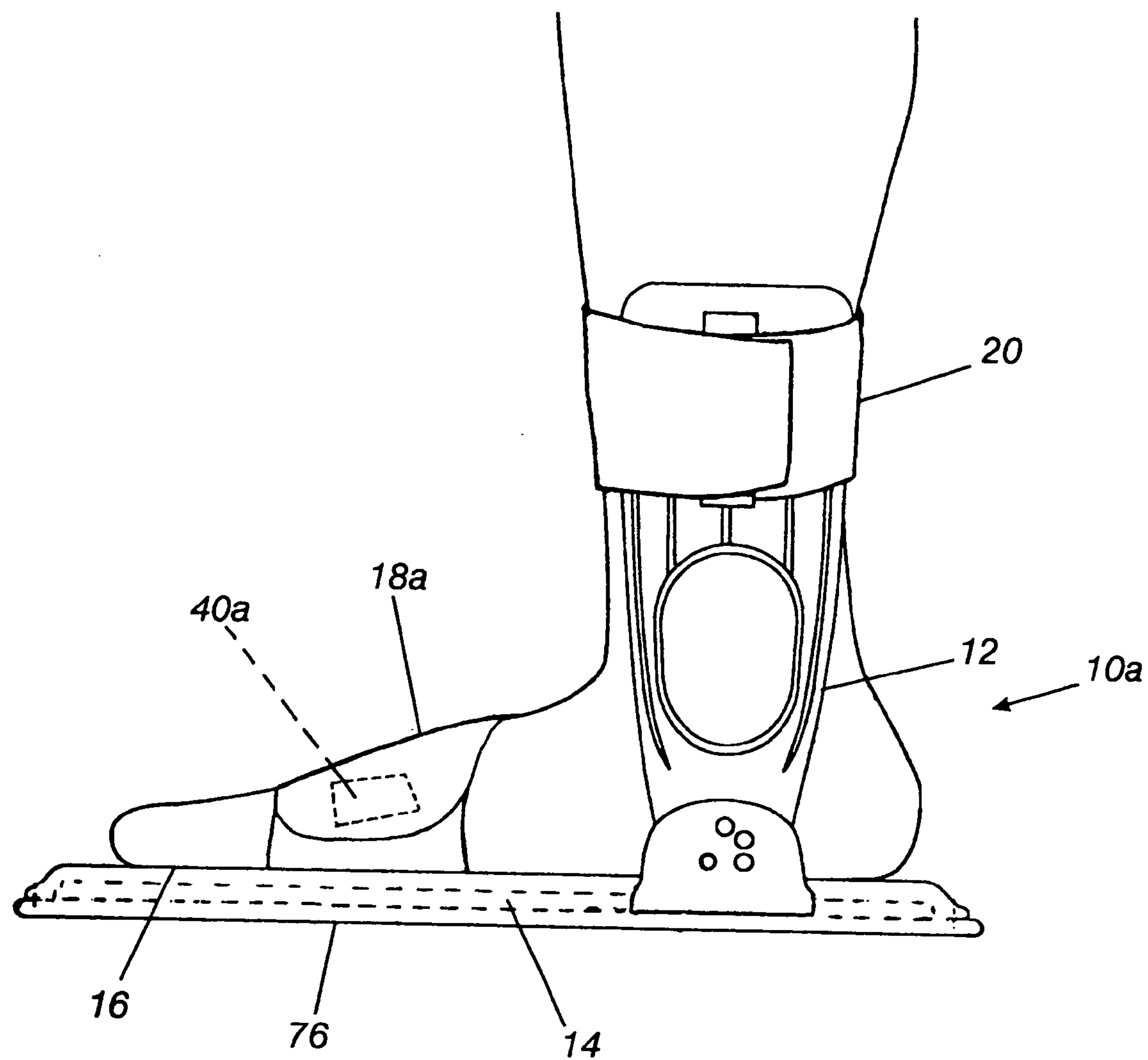
FIG. 5 is a side view of an alternative embodiment of a foot splint, taken from the lateral side of the wearer's foot, in position on the wearer's left foot.

FIG. 5 shows an alternative embodiment of a foot splint **10*a*. The alternative foot splint 10*a* is essentially the same as previously described, except that instead of having a full wrap, the wrap 18*a* is essentially a strap. The wrap 18*a* is pulled over the wearer's foot and secured by complementary Velcro-type hook and pile fasteners 40*a*. The wrap 18*a* serves to hold the wearer's foot along the footplate 14. This open construction, wherein much of the wearer's foot is not enclosed, assists in keeping the foot cool and comfortable. A suitable bottom 76 may be applied to the bottom of the footplate 14 to cushion the environment from the footplate 14**.

Although the foot splint embodiments 10, **10*a* are shown attached to the left foot and having only a lateral strut, the invention is not to be construed as so limited. By configuring the foot splint 10, 10*a* with only a lateral strut 12, great comfort is achieved for the wearer since the lateral strut 12 is positioned away from the wearer's other leg. However, the foot splint 10, 10*a*** may be configured with only a medial strut, or having both a medial and a lateral strut. Without need for further description, one skilled in the subject art would appreciate that the medial strut could be similarly configured to that of the lateral strut.

Referring to FIG. 3, in use, the flap portion 34 is pulled opened to allow easy placement of the wearer's foot onto the insole 16, where it is supported by the footplate 14. The desired degree of dorsiflexion for the foot splint 10 is then set by inserting the set screw 90 (FIG. 4) through corresponding set openings. Thereafter, the wearer secures the foot splint 10 in place on his foot and leg by first pulling the flap 34 over his foot and then securing the strap 70 around his leg. The flap 34 and strap 20 are held in place by Velcro™. The foot splint 10, now secured in place, holds the wearer's ankle in dorsiflexion, causing the wearer's plantar fascia to be held at a slight stretch.

The light weight, low profile, and open configuration of the foot splint 10 allows for the wearer to move vastly unimpeded between sleep positions, resulting in a more restful sleep. Moreover, the footplate 14 and the lateral strut 12 provide sufficient structure to support the foot, yet are positioned on the wearer's foot and leg so that virtually no pressure points are caused to the wearer during periods of sleep. The malleolus opening 82 in the strut 12 further assists in eliminating pressure points by removing rigid structure from near the wearer's ankle. Further, the lateral placement of the strut 12 keeps the rigid portions of the foot splint 10 from inadvertently abrading, striking, or otherwise interfering with the wearer's other leg.

The foot splint 10 is also comfortable since it requires only minimal structure to hold the wearer's foot in place.

Moreover, the soft wrap 18, secures the foot within the foot splint 10 while minimally confining the foot and forming a slipper-like feel for the wearer.

SUMMARY OF THE ACHIEVEMENT OF THE OBJECTS OF THE INVENTION

From the foregoing, it is readily apparent that we have invented an improved foot splint for assisting in the rehabilitation from plantar fasciitis. The foot splint maintains the foot in slight dorsiflexion in order to stretch the plantar fascia. The lateral positioning of the foot splint, and the foot splint's lightweight and non-bulky configuration, make the present invention particularly suitable for wearing in bed during the course of sleep.

It is to be understood that the foregoing description and specific embodiments are merely illustrative of the best mode of the invention and the principles thereof, and that various modifications and additions may be made to the apparatus by those skilled in the art, without departing from the spirit and scope of this invention, which is therefore understood to be limited only by the scope of the appended claims.

What is claimed:

1. A night splint for treating foot and ankle injuries comprising:

a footplate having a lateral side, a medial side, a toe region and a heel region;

a bracket having a pivot, said bracket being integrally attached to said footplate on said medial side at said heel region;

a first strut pivotally attached to said bracket at said pivot, said first strut comprising a plurality of radially spaced set openings to hold a wearer's foot at an angle of dorsiflexion;

a soft wrap adapted to adjustably retain a wearer's foot against said footplate; and a strap adjustably attached to said strut, said strap having sufficient length so that a free end of the strap can be wrapped around the lower leg of a wearer; said strap having corresponding hook and loop fasteners to secure said strap to strut;

wherein said footplate can be adjusted about said pivot and retained at a plurality of predetermined angles by said plurality of radially spaced set openings in order to provide varying degrees of stretch to a plantar fascia ligament, said splint lacking a corresponding second strut on an opposite side of the footplate; and wherein said plurality of radially spaced set openings comprises angle settings of 90, 85 and 80 degrees.

2. A night splint for treating foot and ankle injuries comprising:

a footplate having a lateral side, a medial side, a toe region and a heel region;

a bracket having a pivot, said bracket being integrally attached to said footplate on said medial side at said heel region;

a first strut pivotally attached to said bracket at said pivot, said first strut comprising a plurality of radially spaced set openings to hold a wearer's foot at an angle of dorsiflexion;

a soft wrap adapted to adjustably retain a wearer's foot against said footplate; and a strap adjustably attached to said strut, said strap having sufficient length so that a free end of the strap can be wrapped around the lower leg of a wearer; said strap having corresponding hook and loop fasteners to secure said strap to strut;

wherein said footplate can be adjusted about said pivot and retained at a plurality of predetermined angles by said plurality of radially spaced set openings in order to provide varying degrees of stretch to a plantar fascia ligament, said splint lacking a corresponding second strut on an opposite side of the footplate; and wherein said first strut further includes an opening that coincides with the ankle malleolus when said foot splint is in place on the wearer.

3. The foot splint of claim 2, wherein said first strut further comprises an inward facing surface, and cushioning material disposed thereon.

4. The foot splint of claim 3, wherein said cushioning material substantially encompasses said first strut.

5. A night splint for treating foot and ankle injuries comprising:

a footplate having a lateral side, a medial side, a toe region and a heel region;

a bracket having a pivot, said bracket being integrally attached to said footplate on said medial side at said heel region;

a first strut pivotally attached to said bracket at said pivot, said first strut comprising a plurality of radially spaced set openings to hold a wearer's foot at an angle of dorsiflexion;

a soft wrap adapted to adjustably retain a wearer's foot against said footplate; and a strap adjustably attached to said strut, said strap having sufficient length so that a free end of the strap can be wrapped around the lower leg of a wearer; said strap having corresponding hook and loop fasteners to secure said strap to strut;

wherein said footplate can be adjusted about said pivot and retained at a plurality of predetermined angles by said plurality of radially spaced set openings in order to provide varying degrees of stretch to a plantar fascia ligament, said splint lacking a corresponding second strut on an opposite side of the footplate; and wherein said soft wrap substantially encompasses said footplate.

6. A night splint for treating foot and ankle injuries comprising:

a footplate having a lateral side, a medial side, a toe region and a heel region;

a bracket having a pivot, said bracket being integrally attached to said footplate on said medial side at said heel region;

a first strut pivotally attached to said bracket at said pivot, said first strut comprising a plurality of radially spaced set openings to hold a wearer's foot at an angle of dorsiflexion;

a soft wrap adapted to adjustably retain a wearer's foot against said footplate; and a strap adjustably attached to said strut, said strap having sufficient length so that a free end of the strap can be wrapped around the lower leg of a wearer; said strap having corresponding hook and loop fasteners to secure said strap to strut;

wherein said footplate can be adjusted about said pivot and retained at a plurality of predetermined angles by said plurality of radially spaced set openings in order to provide varying degrees of stretch to a plantar fascia ligament, said splint lacking a corresponding second strut on an opposite side of the footplate; and wherein said soft wrap comprises a comfortable slipper-like enclosure.

7. The foot splint of claim 6, wherein said soft wrap further comprises a cupped heel portion to hold the heel of the wearer's foot.

8. The foot splint of claim 6, wherein said soft wrap further comprises at least one fastener that is capable of adjustably securing the wearer's foot within said slipper-like enclosure.

9. The foot splint of claim 8, wherein said at least one fastener is selected from the group consisting of: hook and loop type fasteners, snaps, zippers, and laces.

10. A night splint for treating foot and ankle injuries comprising:

a footplate having a lateral side, a medial side, a toe region and a heel region;

a bracket having a pivot, said bracket being integrally attached to said footplate on said medial side at said heel region;

a first strut pivotally attached to said bracket at said pivot, said first strut comprising a plurality of radially spaced set openings to hold a wearer's foot at an angle of dorsiflexion;

a soft wrap adapted to adjustably retain a wearer's foot against said footplate; and a strap adjustably attached to said strut, said strap having sufficient length so that a free end of the strap can be wrapped around the lower leg of a wearer; said strap having corresponding hook and loop fasteners to secure said strap to strut;

a soft insole laid over said footplate to provide a cushioning carrier between the wearer's foot and said footplate;

wherein said footplate can be adjusted about said pivot and retained at a plurality of predetermined angles by said plurality of radially spaced set openings in order to provide varying degrees of stretch to a plantar fascia ligament, said foot splint lacking a corresponding second strut on an opposite side of the footplate.

11. The foot splint of claim 10, wherein said strap further comprises at least one fastener that is capable of adjustably fastening said first strut to the lower leg of the wearer.

12. The foot splint of claim 11, wherein said at least one fastener is selected from the group consisting of: hook and loop type fasteners, snaps, zippers, and laces.

13. A night splint for treating foot and ankle injuries comprising:

a footplate having a lateral side, a medial side, a toe region and a heel region;

a bracket having a pivot, said bracket being integrally attached to said footplate on said medial side at said heel region;

a first strut pivotally attached to said bracket at said pivot, said first strut comprising a plurality of radially spaced set openings to hold a wearer's foot at an angle of dorsiflexion;

a soft wrap adapted to adjustably retain a wearer's foot against said footplate; and a strap adjustably attached to said strut, said strap having sufficient length so that a free end of the strap can be wrapped around the lower leg of a wearer; said strap having corresponding hook and loop fasteners to secure said strap to strut;

wherein said footplate can be adjusted about said pivot and retained at a plurality of predetermined angles by said plurality of radially spaced set openings in order to provide varying degrees of stretch to a plantar fascia ligament, said foot splint lacking a corresponding second strut on an opposite side of the footplate; and wherein said first strut further comprises a set opening.

14. The foot splint of claim 13, wherein said plurality of radially spaced set openings and said set opening can be retained in alignment by an insertion pin, a set screw, or a spring loaded detent.

* * * * *